United States Patent
Niwa et al.

(10) Patent No.: US 11,644,458 B2
(45) Date of Patent: May 9, 2023

(54) METHOD FOR PREPARING SPECIMEN FOR ANALYSIS OR OBSERVATION OF SKIN

(71) Applicant: KABUSHIKI KAISHA YAKULT HONSHA, Minato-ku (JP)

(72) Inventors: Daisuke Niwa, Minato-ku (JP); Akemi Imaoka, Minato-ku (JP); Naoki Izawa, Minato-ku (JP); Yasuyuki Takahashi, Minato-ku (JP); Miyuki Kudo, Minato-ku (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 1145 days.

(21) Appl. No.: 16/316,280

(22) PCT Filed: Aug. 31, 2017

(86) PCT No.: PCT/JP2017/031327
§ 371 (c)(1),
(2) Date: Jan. 8, 2019

(87) PCT Pub. No.: WO2018/043636
PCT Pub. Date: Mar. 8, 2018

(65) Prior Publication Data
US 2020/0292525 A1 Sep. 17, 2020

(30) Foreign Application Priority Data
Aug. 31, 2016 (JP) .............................. JP2016-168718

(51) Int. Cl.
*G01N 33/50* (2006.01)
*G01N 1/04* (2006.01)
*C12Q 1/04* (2006.01)

(52) U.S. Cl.
CPC .............. *G01N 33/50* (2013.01); *C12Q 1/04* (2013.01); *G01N 1/04* (2013.01)

(58) Field of Classification Search
None
See application file for complete search history.

(56) References Cited

U.S. PATENT DOCUMENTS

| 6,203,900 B1 * | 3/2001 | Saika ....................... C12Q 1/04 428/350 |
| 2009/0088434 A1 | 4/2009 | Mayer |

FOREIGN PATENT DOCUMENTS

| JP | 63-106558 A | 5/1988 |
| JP | 1-250223 A | 10/1989 |
| JP | 7-138143 A | 5/1995 |
| JP | 7-316488 A | 12/1995 |
| JP | 07316488 A * | 12/1995 |
| JP | 2000-302632 A | 10/2000 |
| JP | 2002-318230 A | 10/2002 |
| JP | 3868345 B2 | 1/2007 |
| JP | 2009-510023 A | 3/2009 |
| JP | 2014-73977 A | 4/2014 |
| WO | WO 2007/039533 A2 | 4/2007 |

OTHER PUBLICATIONS

EngMT—Furuse, K. et al. Composition used for painting skin or container. Japanese Patent Application Publication No. JP-07316488; Date of Publication: May 12, 1995. pp. 1-7; specif, pp. 3, 4, 5 (Year: 1995).*
Leiwei Chemical Company Ltd. PVA 105 & PVA 205. Datasheet [online]. Copyright 2008 Leiwei Chemical Co. Ltd. Retrieved from the internet: Apr. 6, 2022. Downloaded from the interent: <www.polyvinyl-alcohol.net/PVA-105-205.html> pp. 1-2.*
Korean Office Action dated Jul. 15, 2021 in Korean Application No. 10-2019-7004046 (with English translation), citing document AX therein, 11 pages.
A.Hambraeus et al., "Skin sampling-validation of a pad method and comparison with commonly used method", Journal of Hospital Infection, vol. 16, 1990, pp. 19-27 (9 total pages).
Office Action dated Feb. 24, 2021 in corresponding Japanese Patent Application No. 2018-537391 (with English Translation), citing document AX therein, 12 pages.
Epilation clip[online], The reason why "treatment of waste hair with Brazilian wax" is damaging, Internet Archive: Wayback Machine, publication date : Sep. 9, 2015, [search date : Feb. 11, 2021], <https://web.archive.org/web/20150909015106/https://datsumo-clip.com/mudage-goods/80/> (with machine translation).
Written Opinion dated Jun. 11, 2020 in Singaporean Patent Application No. 11201811521S, citing document AO therein, 7 pages.
Extended European Search Report dated Mar. 23, 2020 in corresponding European Patent Application No. 17846640.5, citing documents AO and AP therein, 7 pages.
International Search Report dated Nov. 28, 2017 in PCT/JP2017/031327 filed Aug. 31, 2017.

(Continued)

*Primary Examiner* — Renee Claytor
*Assistant Examiner* — Sharon M. Papciak
(74) *Attorney, Agent, or Firm* — Oblon, McClelland, Maier & Neustadt, L.L.P.

(57) ABSTRACT

A method is shown for preparing a specimen for extensively analyzing a resident skin bacterium and/or a substance present in the stratum corneum, such as a protein or a lipid, or observing the shape of the stratum corneum. A method for preparing a specimen for analyzing a resident skin bacterium and/or a substance present m the stratum corneum or observing the shape of the stratum, includes applying a solution containing a polyvinyl alcohol polymer to the skin so as to form a thin-film and peeling and collecting the formed thin-film.

15 Claims, 2 Drawing Sheets
Specification includes a Sequence Listing.

(56) References Cited

OTHER PUBLICATIONS

Elizabeth K. Costello, et al., "Bacterial Community Variation in Human Body Habitats Across Space and Time," Science, vol. 326, Dec. 18, 2009, 5 Pages.
B. Lange-Asschenfeldt, el al., "Distribution of Bacteria in the Epidermal Layers and Hair Follicles of the Human Skin," Skin Pharmacology and Physiology, vol. 24, 2011, pp. 305-311.

* cited by examiner

[Figure 1]
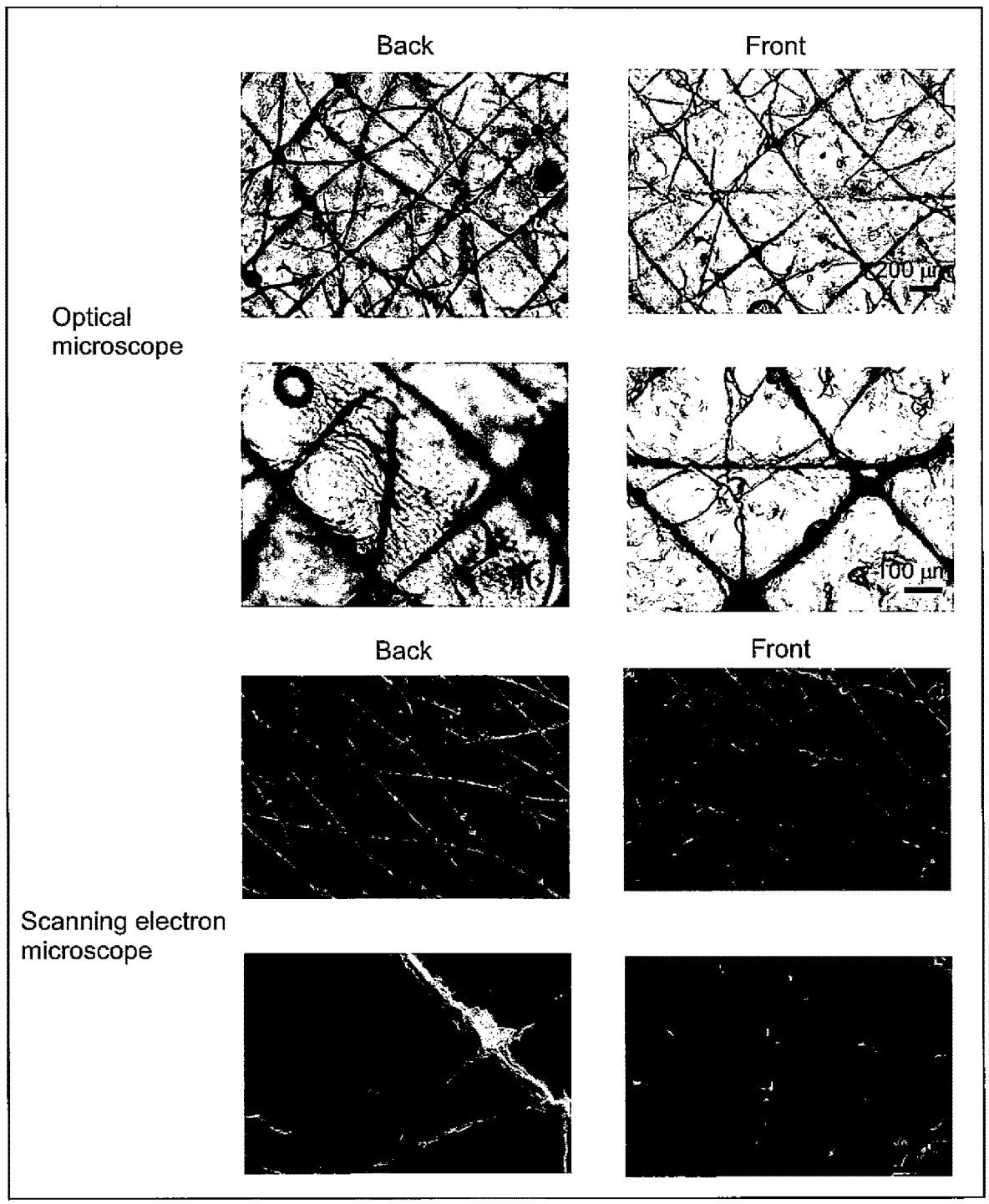

[Figure 2]
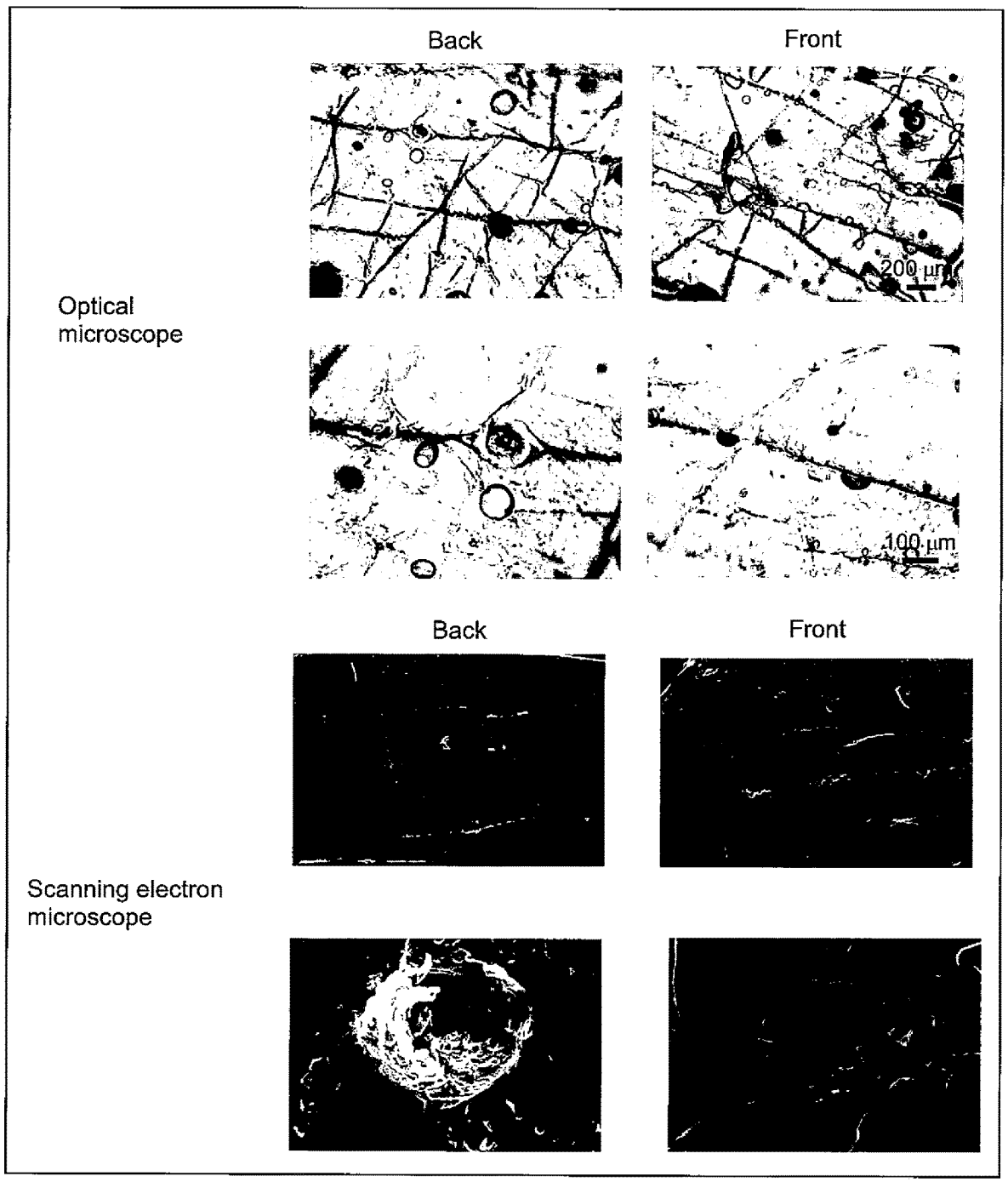

METHOD FOR PREPARING SPECIMEN FOR ANALYSIS OR OBSERVATION OF SKIN

TECHNICAL FIELD

The present invention relates to a method for preparing a specimen for analysis or observation of the skin. More specifically, the invention relates to a method for preparing a specimen for analyzing a resident skin bacterium and/or a substance present in the stratum corneum or observing the shape of the stratum corneum.

BACKGROUND ART

In recent years, the influence (e.g., usefulness) on the skin by resident skin bacteria has attracted attention. The resident skin bacteria are microorganisms present on the skin, and use sweat, sebum, etc. as nutrient sources. These resident skin bacteria usefully work, for example, suppress the growth of pathogenic bacteria and molds when balanced on the skin, but abnormally grow due to stress, etc. and adversely affect the skin in some cases. For example, if secretion of sebum and pore clogging simultaneously occur, acne bacteria abnormally grow and cause pimples. Accordingly, analysis of resident bacteria on the skin or a substance present in the stratum corneum, such as sebum, serving as a nutrient source for the bacteria or objective grasp of the shapes of both sides of collected stratum corneum, such as sulcus cutis, crista cutis, texture, pore, and wrinkle, is very important for investigation of causes of skin troubles and development of cosmetics. In addition, if various metabolites (for example, glycerol and free fatty acids) produced by resident skin bacteria and the resident bacteria can be simultaneously collected, it is probably very useful for investigation of the mechanism of the usefulness of these bacteria.

Conventionally, resident skin bacteria and stratum corneum are collected mainly using a swab method (Non-Patent Literature 1) or a tape stripping method (Non-Patent Literature 2). The swab method is a method for collecting a specimen by wiping a skin surface with, for example, a swab to capture resident bacteria or stratum corneum thereon and rinsing the swab with a solvent; and the tape stripping method is a method involving affixing adhesive tape on the skin, and collecting resident bacteria or stratum corneum attached to the tape.

However, the swab method has problems, such that the applying force varies depending on the collector, there is a risk of causing insufficient wiping, and all the bacteria attached to the swab cannot be rinsed out, and it is not certain whether the bacteria can be stably collected. In addition, collectable specimens are limited, such that the collection rates of components on the skin are also low in addition to that of bacteria and that collection of stratum corneum is unsatisfactory.

In the tape stripping method, the adhesive component of the tape to be used is not generally disclosed, some cases need to use an organic solvent for collecting the bacteria attached to the tape, and it is impossible to collect resident skin bacteria in a living state. In addition, it is conceived that some adhesives cause harm to the living body from which a specimen is collected or to the bacteria to be collected. In addition, since the tape includes a support, there are problems such that a gap is formed when bacteria or stratum corneum are collected from a curved portion and thus the collection rate is reduced, and that the range allowing collection is limited by the width of the tape.

In addition, although the tape stripping method can collect stratum corneum, only the outermost one or several layers among a plurality of layers can be collected. Accordingly, this method also has a risk of being unable to collect a specimen in an amount sufficient for analysis of components in the stratum corneum.

In addition, as a method for measuring the area and volume of keratinocytes, a method involving affixing, on the skin, a keratinocyte-sampling tool having a support coated with a water-soluble binder containing a vinyl pyrrolidone-vinyl acetate copolymer, and then collecting keratinocytes from the binder has been reported (Patent Literature 1).

However, since the method is for collecting keratinocytes without impairing the volume shape and uses a protease or a surfactant for dispersing the keratinocytes, the method is not recognized as a method for preparing a specimen for analyzing resident skin bacteria in a living state. In addition, since a support is used, there are problems that the polymer remains on the support and thus the quantitativity is not guaranteed and that the method is not suitable for collecting a specimen from a curved part.

Furthermore, since the vinyl pyrrolidone-vinyl acetate copolymer has low solubility in aqueous solvents and needs to use an organic solvent, such as ethanol, to be applied to the skin, it is impossible to collect resident skin bacteria in a living state; and since the vinyl pyrrolidone-vinyl acetate copolymer alone has a low viscosity and low film formability, it is necessary to add a component for increasing the viscosity, such as hydroxypropyl methylcellulose, for application to the skin, and it is also concerned that such a component has a risk of inhibiting the analysis of a specimen.

CITATION LIST

Patent Literature

Patent Literature 1: JP-B-3868345

Non-Patent Literature

Non-Patent Literature 1: Costello, et al., Bacterial community variation in human body habitats across space and time. Science, 326, 1694-1697, 2009

Non Patent Literature 2: B. Lange-Asschenfeldt, el al., Distribution of bacteria in the epidermal layers and hair follicles of the human skin. Skin Pharmacol. Physiol., 24, 305-311, 2011

SUMMARY OF INVENTION

Technical Problem

The present invention relates to providing a method for preparing a specimen for extensively analyzing resident skin bacteria and/or a substance present in the stratum corneum, such as a protein or a lipid, or for observing the shape of the stratum corneum.

Solution to Problem

The present inventors have studied in view of the above problems and have found that when a solution containing a polyvinyl alcohol polymer is applied to the skin to form a thin-film, resident skin bacteria in the thin-film can be collected in a living state and a substance contained in the stratum corneum can be efficiently collected, that the use of this allows analysis of resident skin bacteria and various substances present in the stratum corneum, and that the shapes of both sides of the collected stratum corneum can be accurately observed.

That is, the present invention relates to the following aspects 1) to 12):

1) A method for preparing a specimen for analyzing a resident skin bacterium and/or a substance present in the stratum corneum or observing the shape of the stratum corneum, comprising applying a solution containing a polyvinyl alcohol polymer to the skin so as to form a thin-film and peeling and collecting the formed thin-film;

2) The method according to 1), wherein the resident skin bacterium comprises a live bacterium;

3) The method according to 1) or 2), wherein the substance present in the stratum corneum comprises one or more selected from the group consisting of proteins, amino acids, lipids, nucleic acids, saccharides, vitamins, hormones, and peptides;

4) The method for preparing a specimen for observing the shape of the stratum corneum according to 1), further comprising immobilizing the peeled and collected thin-film to a support for microscopic observation, dissolving and removing the polyvinyl alcohol polymer, and then performing drying;

5) The method according to 4), wherein the immobilization is performed by affixing the thin-film to an immobilizing agent applied to the support for microscopic observation;

6) The method according to any one of 1) to 5), wherein the polyvinyl alcohol polymer is a polyvinyl alcohol polymer having a degree of saponification of 70 to 99 mol %;

7) The method according to any one of 1) to 6), wherein the polyvinyl alcohol polymer is a polyvinyl alcohol polymer having a degree of polymerization of 50 to 3,000;

8) The method according to any one of 1) to 7), wherein the polyvinyl alcohol polymer is a polyvinyl alcohol polymer having a viscosity (4% aqueous solution, temperature: 20° C.) of 4 to 60 mPa·s;

9) The method according to any one of 1) to 8), wherein the solution containing the polyvinyl alcohol polymer is a 10 to 30 mass % polyvinyl alcohol polymer solution;

10) The method according to any one of 1) to 9), wherein the solution containing the polyvinyl alcohol polymer is applied to the skin and is then left at room temperature for 20 minutes or more;

11) A specimen for skin analysis or observation, which is prepared by the method according to any one of 1) to 10); and 12) A method for observing the shape of the stratum corneum, comprising microscopic observation using the specimen for skin observation prepared by the method according to 4) or 5).

Advantageous Effects of Invention

According to the method of the present invention, resident skin bacteria can be collected in a living state with minimal invasion and with ease regardless of the body part, and a substance present in the stratum corneum can be efficiently collected. In addition, the conditions of both sides of the collected stratum corneum, such as sulcus cutis, crista cutis, texture, pore, wrinkle, and the depth of the collected stratum corneum, can be accurately observed.

BRIEF DESCRIPTION OF DRAWINGS

FIG. 1 shows microscopic observation images of the front and back of the stratum corneum collected from the antebrachial region.

FIG. 2 shows microscopic observation images of the front and back of the stratum corneum collected from the forehead.

DESCRIPTION OF EMBODIMENTS

The method for preparing a specimen for skin analysis or observation of the present invention is a method for preparing a specimen for analyzing resident skin bacteria or a substance present in the stratum corneum or observing the shape of the stratum corneum, and comprises applying a solution containing a polyvinyl alcohol polymer to the skin so as to form a thin-film and peeling and collecting the formed thin-film.

One example of the target of skin analysis of the present invention is resident skin bacteria. The term "resident skin bacteria" means bacteria growing on human skin, and the species of the bacteria is not particularly limited in the present invention. Although it is thought that individual differences, site differences, seasonal variations, and so on, are seen in the type of resident skin bacteria, acne bacteria (*Propionibacterium acnes*) live as most predominant anaerobic bacteria, and *Staphylococcus aureus* and *Staphylococcus epidermidis* bacteria live as aerobic bacteria. It is known that resident skin bacteria have a relationship with biological defense from other pathogenic microorganisms and with disease expression and that if the balance of resident skin bacteria is disrupted by poor systemic conditions due to, for example, an external wound or a disease, psychological stress, coldness, dryness, unsuitable washing, etc., *Staphylococcus aureus, Propionibacterium acnes*, and other bacteria excessively grow to induce various cutaneous symptoms and cause disease expression. It is also known that useful bacteria, such as *Staphylococcus epidermidis*, decompose sebum and produce glycerol and free fatty acids and are therefore effective for moisture retention and also maintain the skin acid and suppress growth of mold and so on. According to the present invention, resident skin bacteria including *Propionibacterium acnes, Staphylococcus aureus*, and *Staphylococcus epidermidis* can be collected in a living state.

Examples of the target of the skin analysis of the present invention further include substances present in the stratum corneum. The substances present in the stratum corneum are substances present on the stratum corneum surface (skin surface) or in the stratum corneum, and the origin and type thereof are not particularly limited. Specifically, in addition to the stratum corneum components such as keratin and filaggrin, stratum corneum intercellular lipid components such as ceramide and cholesterol, cytokines such as interleukins, proteins such as chemokines and enzymes, metabolites of resident skin bacteria, sebum secreted from the sebaceous gland, lipids, fatty acids, and hormones are encompassed.

Examples of the metabolite of resident skin bacteria include various metabolites decomposed and produced by resident skin bacteria from substances, such as proteins and lipids, present in the stratum corneum. Specifically, the examples include triglycerides, diglycerides, fatty acids, and glycerol decomposed and produced from sebum.

Examples of the substance present on the stratum corneum (skin) surface include, in addition to components of perspiration secreted from the apocrine gland or eccrine gland and plasma, amino acids and peptides. Among these components, in particular, it is preferable to include one or more of proteins, amino acids, lipids, nucleic acids, saccharides, vitamins, hormones, and peptides because these can function as indicators of skin characteristics and are readily affected by the distribution of resident skin bacteria.

According to the method of the present invention, the resident skin bacteria can be collected, and also a substance present in the stratum corneum can be collected. In addition, since resident skin bacteria including live and dead bacteria can be collected in the state as they are present on the skin, it is possible to clarify the variety thereof forming flora on the skin and the existing form thereof.

Examples of the target of the skin observation of the present invention include the shape of the stratum corneum.

That is, it is possible to observe the microstructure of the stratum corneum surface, for example, the conditions of sulcus cutis (width, tilt angle, and density), the conditions of crista cutis (i.e., texture) surrounded by sulcus cutis, the size of pores, wrinkles, and the depth of collected stratum corneum, as conditions viewed from the outside of the skin by microscopic observation with the specimen for skin observation of the present invention.

In the preparation of a specimen for skin analysis or observation of the present invention, a solution containing a polyvinyl alcohol (PVA) polymer (PVA polymer solution) is applied to the skin so as to form a thin-film.

Here, the PVA polymer is a polymeric material having [$CH_2CH(OH)$] as a unit structure and is usually produced by saponification of polyvinyl ester. As the polyvinyl ester, for example, vinyl formate, vinyl acetate, vinyl propionate, vinyl butyrate, vinyl caprate, vinyl laurate, vinyl palmitate, and vinyl stearate can be used alone or in combination, and vinyl acetate is preferably used.

In addition, the PVA polymer of the present invention may have a functional group other than a hydroxyl group, and examples of the functional group other than a hydroxyl group include an amino group, a thiol group, a carboxyl group, a sulfone group, a phosphate group, a carboxylate group, a sulfonate ion group, a phosphate ion group, an ammonium group, a phosphonium group, a silyl group, a siloxane group, an alkyl group, an allyl group, a fluoroalkyl group, an alkoxy group, a carbonyl group, and a halogen group.

The PVA polymer of the present invention preferably has a degree of saponification of 70 to 99 mol %, more preferably 75 to 95 mol %, and even more preferably 86.5 to 89.0 mol %. Here, the degree of saponification of the PVA polymer is mol percent (mol %) of the hydroxyl group obtained by saponification of polyvinyl ester, i.e., hydrolysis, and is a value measured by a method in accordance with JIS K6726.

The PVA polymer of the present invention preferably has a degree of polymerization of 50 to 3,000, more preferably 500 to 2,500, and even more preferably 600 to 2,400 from the viewpoints of thin-film formation and the collection rate of a target for analysis or observation. The degree of polymerization of the PVA polymer is measured in accordance with JIS K6726.

In general, the difference in the degree of polymerization can be substituted with the viscosity at a certain concentration (usually 4% aqueous solution, 20° C.). The PVA polymer of the present invention preferably has a viscosity of 4 to 60 mPa·s and more preferably 4.5 to 52 mPa·s. Here, the viscosity is a value calculated with a Hoppler viscometer using a 4% aqueous solution under the condition of a temperature of 20° C.

In addition, the PVA polymer of the present invention preferably has an average molecular weight of 2,200 to 132,000 and more preferably 20,000 to 110,000.

Commercially available examples of the PVA polymer that can be used in the present invention include various grades of trade name "Gohsenol" series manufactured by The Nippon Synthetic Chemical Industry Co., Ltd., such as EG-40 (viscosity (4%, 20° C.): 40.0-46.0 mPa·s, degree of saponification: 86.5-89.0 mol %, degree of polymerization: 2400), EG-25 (viscosity (4%, 20° C.): 20.5-24.5 mPa·s, degree of saponification: 86.5-89.0 mol %, degree of polymerization: 1800), and EG-05 (viscosity (4%, 20° C.) 4.8-5.8 mPa·s, degree of saponification: 86.5-89.0 mol %, degree of polymerization: 600).

Although such PVA polymers can be used alone, a mixture of PVA polymers having different degrees of saponification or polymerization and/or different viscosities may be used. The use of a mixture of PVA polymers having different degrees of saponification or polymerization and/or different viscosities can change the viscosity and can change the degree of adhesion to the skin. In addition, from the viewpoint of thin-film formation, it is preferred to use one or more PVA polymers having a degree of polymerization of 1,500 or more.

The content of the PVA polymer in a solution containing the PVA polymer (PVA polymer solution) varies depending on the molecular weight and the degree of saponification of the PVA and is, from the viewpoints of preventing dripping of the applied solution and ease in drying, usually a concentration of 10 to 30 mass %, preferably 12 to 25 mass %, more preferably 15 to 25 mass %, and particularly preferably 15 to 22 mass %.

In addition, the solvent of the solution is preferably water, a phosphate buffer, or physiological saline, and water is particularly preferred. The solution can contain ethanol within a range that does not affect the resident skin bacteria and the substance present in the stratum corneum. In such a case, the content of the ethanol is preferably 0 to 20 mass % and more preferably 0 to 5 mass %. If the live resident skin bacteria need to be collected, it is preferable to use a solvent not containing ethanol. In addition, it is important not to add an additive containing, for example, a solid substance, a protein, an amino acid, or a lipid, to the PVA polymer solution, for avoiding a risk of hindering the subsequent analysis. Accordingly, the PVA polymer solution contains a PVA polymer and a solvent only.

The PVA polymer solution may be applied to the skin so as to form a thin-film on the skin surface and is, for example, applied in such a manner that the solution is uniformly and continuously attached to the skin surface. Although the method of the application is not particularly limited, it is preferable to use a hygienic spatula or to directly apply a PVA polymer solution contained in a tube.

The PVA polymer solution applied to the skin is usually dried by being left at room temperature for about 20 to 40 minutes and is formed into a thin-film. Here, the thin-film has a thickness of 0.03 to 0.5 mm and preferably 0.04 to 0.2 mm.

Although the time of being left may be a period allowing formation of a thin-film, from the viewpoint of sufficiently collecting resident skin bacteria or a substance present in the stratum corneum, it is preferable to leave the solution usually at room temperature for 20 minutes or more, preferably for 20 to 40 minutes, and more preferably for 20 to 35 minutes.

The formed thin-film is peeled from the skin and is appropriately treated according to the subsequent analysis or observation. That is, in the case of a specimen for analysis of resident skin bacteria or analysis of stratum corneum components, the thin-film is dissolved in an aqueous solvent, such as water, physiological saline, PBS, or Ringer's solution or in an organic solvent, such as methanol, ethanol, ethyl acetate, acetone, chloroform, or diethyl ether, to extract the specimen, which can be supplied to analysis by a method similar to tape stripping. In particular, in order to analyze live resident skin bacteria, it is preferable that the thin-film be dissolved in an aqueous solvent, in particular, physiological saline or PBS. In addition, in order to prevent denaturation of the specimen, it is preferable to perform the analysis at room temperature or less.

As described above, in the peeled thin-film prepared by the present invention, resident skin bacteria living in the skin can be collected in a living state, and also since multiple layers of stratum corneum can be simultaneously collected, a substance present in the stratum corneum can be efficiently collected. Accordingly, the peeled thin-film can be used as a specimen for analyzing resident skin bacteria in a living state or as a specimen for analyzing a substance present in the stratum corneum. For example, resident skin bacteria, metabolites of resident skin bacteria present in the stratum corneum, organism-derived proteins, such as cytokines, and enzymes, such as lipase and protease, present in the stratum corneum are collected using the present invention and can be used, for example, for identifying the type and amount of the resident bacteria, metabolites, or organism-derived proteins to verify the relationship with the skin conditions, isolating a novel resident skin bacterium to identify the properties thereof, diagnosing the skin conditions, and analyzing the skin conditions before and after application of a cosmetic, a medicine or the like. In addition, since, according to the present invention, a substance present in the stratum corneum can be efficiently collected, the solution containing the specimen does not need to be concentrated, and analysis can be efficiently performed.

Various analyses using the specimen prepared by the present invention can be performed using an appropriate known method according to the purpose. For example, DNA is extracted from a solution prepared by dissolving a specimen of the present invention in an aqueous solvent, and the amount of target resident skin bacteria is measured using a nucleic acid amplification technique; resident skin bacteria are comprehensively analyzed by a 16S metagenome analysis method using a next-generation sequencer; live bacteria inoculated in a medium, such as GAM agar medium, is measured; the ratio of live bacteria to dead bacteria is measured; the amount of proteins is measured by, for example, a BCA protein assay; fatty acids are analyzed by gas chromatography; ionic metabolites on the skin are comprehensively analyzed using, for example, CE-TOF MS; cytokines in the stratum corneum are comprehensively analyzed using a kit such as Milliplex; or a part of the peeled thin-film is directly cut out with a laser by a laser microdissection method and is collected to acquire genetic information of resident skin bacteria present at a specific position on the skin.

When the formed thin-film is used as a specimen for observing the shape of the stratum corneum, in the observation of the peeled and collected thin-film from the front side, the stratum corneum side of the collected specimen is immobilized to a support for microscopic observation; the polyvinyl alcohol polymer is dissolved and removed; and then drying is performed to provide a specimen for microscopic observation. In the observation of the back side, the polyvinyl alcohol side of the collected specimen is immobilized to a support for microscopic observation, and then drying is performed to provide a specimen for microscopic observation.

Here, examples of the support for microscopic observation include supports of, for example, a metal, a silicon substrate, a slide glass, a dish, or a petri dish, and a transparent support, such as a slide glass, a dish, or a petri dish, is preferred, and a slide glass is more preferred.

The immobilization of a thin-film to such a support can be performed by, for example, affixing the thin-film to an immobilizing agent applied to the support.

The immobilizing agent may be any water-insoluble compound that adheres to a support and can immobilize the stratum corneum structure in a thin-film, and a transparent compound is preferred, and examples thereof include organic adhesives of, for example, thermoplastic resins (vinyl acetate resins, polyvinyl acetal, ethylene-vinyl acetate resins, vinyl chloride resins, acrylic resins, polyamide, cellulose, and α-olefin), thermosetting resins (urea resins, melamine resins, phenolic resins, resorcinol resins, epoxy resins, structural acrylic resins, polyester, polyurethane, and polyaromatic resins), and elastomers (chloroprene rubber, nitrile rubber, styrene butadiene rubber, polysulfide, butyl rubber, silicone rubber, acrylic rubber, modified silicone rubber, urethane rubber, silylated urethane resins, and telechelic polyacrylate).

It is possible to observe the conditions of the microstructure of the stratum corneum surface from the outside of the skin using the thus-prepared specimen for microscopic observation by performing the observation with, for example, an optical microscope or an electron microscope.

EXAMPLES

Example 1: Preparation of Specimen

Fifteen grams of each of two types of polyvinyl alcohol, EG-40 (viscosity (4%, 20° C.): 40.0-46.0 mPa·s, degree of saponification: 86.5-89.0 mol %, degree of polymerization: 2400, manufactured by The Nippon Synthetic Chemical Industry Co., Ltd.) and EG-25 (viscosity (4%, 20° C.): 20.5-24.5 mPa·s, degree of saponification: 86.5-89.0 mol %, degree of polymerization: 1800, manufactured by The Nippon Synthetic Chemical Industry Co., Ltd.), were added to 100 g of water heated to 80° C., and 20 g of ethanol was then added thereto, followed by mixing to prepare a PVA solution (20 mass %).

The prepared PVA solution (400 µL) was applied to a part (4 cm$^2$) of the left forehead. After drying at room temperature for about 30 minutes, the formed thin-film was peeled. The peeled thin-film was immersed in 2 mL of PBS and was left overnight at 4° C. and was then stirred with a vortex mixer to obtain an inventive specimen 1. The same operation was performed for three subjects.

Comparative Example 1 (Swab Method)

A swab was reciprocated 25 times on a part (4 of the right forehead. The tip of the swab was immersed in 1 mL of PBS and was left overnight at 4° C. and was then stirred with a vortex mixer to obtain a comparative specimen 1. The same operation was performed for three subjects.

Test Example 1: Detection of Resident Skin Bacteria (1) Detection of *Propionibacterium acnes* (Acne Bacteria)

The amounts of acne bacteria in the inventive specimen 1 and the comparative specimen 1 prepared above were measured by the following method.

First of all, the inventive specimen 1 was subjected to centrifugation treatment (15,000 rpm, 10 min), and 1 mL of PBS was added to the resulting precipitate, followed by stirring with a vortex mixer. The same centrifugation treatment as above was performed for washing. The resulting precipitate was dispersed in 200 µL of PBS. One hundred microliters of PBS was added to 100 µL of the dispersion, and 250 µL of a lysis buffer (200 mM Tris-HCl (pH 9.0), 80 mM EDTA (pH 9.0)) and 50 µL of a 10% SDS solution were further added thereto. Subsequently, freezing and thawing were repeated three times, and boiling at 100° C. and then cooling to room temperature were performed. Five hundred microliters of TE-saturated phenol and 300 mg of glass beads were added thereto, and a pulverization with a tissue/cell-disrupting apparatus (Fast Prep) was performed at 5.0 m/s for 30 seconds. Centrifugation was performed at 15,000 rpm for 5 minutes, and 400 µL of the aqueous layer was transferred to another tube. Four hundred microliters of phenol/chloroform/isoamyl alcohol (25:24:1) was added thereto, followed by shaking with Fast Prep at 4.0 m/s for 45 seconds. Subsequently, centrifugation was performed at 15,000 rpm for 5 minutes to collect 250 µL of the aqueous layer. Twenty-five microliters of 3 M sodium acetate (pH 5.4) and 300 µL of isopropanol were added to the resulting aqueous layer, and inversion mixing was performed, followed by leaving at −30° C. for 5 minutes. After centrifugation at 15,000 rpm for 5 minutes, the supernatant was removed, and 500 µL of 70% ethanol was added to the precipitate. After centrifugation at 15,000 rpm for 5 minutes, the supernatant was removed, followed by air drying. The resulting extracted DNA was dissolved in 50 µL of pure water (Milli-Q water). The PCR reagent used was SYBR (registered trademark) Premix Ex Taq (registered trademark) II (Tli RNaseH Plus) (manufactured by TaKaRa Bio Inc.). The sequences of the primers are shown in Table 1. The PCR conditions were one cycle at 95° C. for 5 minutes and 40 cycles of a set of reactions at 95° C. for 15 seconds and at 60° C. for 1 minute.

The comparative specimen 1 was subjected to centrifugation treatment (15,000 rpm, 10 minutes), the resulting precipitate was dispersed in 200 µL of PBS, and the amount of acne bacteria was measured using 100 µL of the dispersion by the same method as that in the inventive specimen 1.

TABLE 1

| Target | Primer name | Sequence | SEQ ID NO |
|---|---|---|---|
| P. acnes | Primer F | 5'-GCGTGAGTGACGGTAATGGGTA-3' | 1 |
|  | Primer R | 5'-TTCCGACGCGATCAACCA-3' | 2 |

(2) Results

The results are shown in Table 2. The results are average values when the operations of Example 1 and Test Example 1 were performed three times in total on different days. Three subjects were denoted as A to C, respectively. It is known that bacteria are present to the same extent on the left and right sides of the face (Literature: J. Clinical Microbiology, 48, 3575-3581, 2010). Accordingly, it was confirmed by Table 2 that the inventive specimen 1 can collect acne bacteria (total number including live bacteria and dead bacteria) to the same extent or more than that in the comparative specimen 1 collected by the swab method.

TABLE 2

| | $Log_{10}$ (Number of bacteria/cm$^2$) | A | B | C |
|---|---|---|---|---|
| Comparative specimen 1 (Swab method) | average | 2.16 | 3.93 | 4.44 |
| Inventive specimen 1 | average | 2.20 | 4.70 | 4.80 |

Example 2: Preparation of Specimen

EG-40 and EG-25 of 2.625 g each were added to 24.75 g of water heated to 80° C. to prepare a PVA solution (PVA: 17.5 mass %).

One hundred and fifty microliters of the PVA solution was applied to each of the left forehead (9 cm$^2$) and the right forehead (9 cm$^2$). After drying for about 30 minutes, the formed thin-films were peeled. The peeled thin-films were each immersed in 600 µL of physiological saline and were shaken at room temperature with a shaker MICRO TUBE MIXER MT-400 (manufactured by Tomy Seiko Co., Ltd.) for 1 hour to obtain an inventive specimen 2.

Test Example 2: Quantitativity for Resident Skin Bacteria (1) Quantitativity for Acne Bacteria The amount of acne bacteria in the inventive specimen 2 prepared above was measured by the following method.

An aliquot of 200 µL of the inventive specimen 2 was added to 200 µL of physiological saline, and centrifugation was performed at 15,000 rpm for 20 minutes to remove the supernatant. Four hundred microliters of physiological saline was added to the resulting precipitate, and the same centrifugation operation was repeated. The resulting precipitate was dispersed in 200 µL of PBS. DNA was extracted by the same method as that in Test Example 1 using 100 µL of the dispersion and was dissolved in 50 µL of pure water (Milli-Q water). The number of acne bacteria in the specimen was measured by the same method (PCR) as that in Test Example 1.

(2) Results

The acne bacteria collected were 3.20 ($Log_{10}$ (number of bacteria/cm$^2$)) in the left forehead and 3.14 ($Log_{10}$ (number of bacteria/cm$^2$)) in the right forehead, and it was confirmed that the numbers of the bacteria collected from the left forehead and the right forehead were almost the same. As described above, since it is known that bacteria are present to the same extent on the left and right sides of the face, it was confirmed that the inventive specimen 2 has a high possibility of quantitatively collecting resident skin bacteria (the total number including live bacteria and dead bacteria).

Example 3: Preparation of Specimen

One hundred and fifty microliters of a PVA solution (PVA: 17.5%) prepared as in Example 2 was applied to a part (9 cm$^2$) of the right cheek. After drying for about 30 minutes, and the peeled thin-film was immersed in 600 µL of physiological saline and was shaken for 30 minutes to obtain an inventive specimen 3.

Comparative Example 2 (Swab Method)

A swab was reciprocated 25 times on a part (9 cm$^2$) of the left forehead. The tip of the swab was immersed in 1 mL of PBS and was shaken for 15 minute to obtain a comparative specimen 2.

Test Example 3: Quantitativity for Live Bacteria (1) Quantitativity for Total Number of Live Bacteria Operation of further addition of 600 μL of physiological saline to the inventive specimen 3, centrifugation at 15,000 rpm for 10 minutes, and removal of 600 μL of the supernatant was repeated twice, and then all the supernatant was removed. Lastly, washing (15,000 rpm, 10 min) with 600 μL was performed again, the supernatant was removed, and the precipitate was then dispersed in 100 μL of physiological saline. The dispersion was diluted 100-fold with physiological saline, and 25 μL thereof was seeded on each GAM agar medium, followed by culturing for 3 days at 37° C. This method can nonselectively measure live bacteria.

The comparative specimen 2 was centrifuged at 15,000 rpm for 10 minutes, and the precipitate was collected and was then dispersed in 100 μL of physiological saline. The dispersion was diluted with physiological saline as in the inventive specimen 3, and the same operation was then performed.

(2) Results

The number of bacteria was 3.15 ($Log_{10}$ (number of bacteria/$cm^2$)) in the inventive specimen 3 and was 3.45 ($Log_{10}$ (number of bacteria/$cm^2$)) in the comparative specimen 2. Accordingly, the present invention and the swab method were able to collect resident skin bacteria (live bacteria) to the same extent.

Example 4: Preparation of Specimen

One hundred and fifty microliters of a PVA solution (PVA: 17.5%) prepared as in Example 2 was applied to a part (9 $cm^2$) of the left cheek. After drying for about 30 minutes, the peeled thin-film was immersed in 600 μL of physiological saline and was shaken for 30 minutes to obtain an inventive specimen 4.

Test Example 4: Fatty Acid Analysis (1) Eighty microliters of the inventive specimen 4 was diluted 5-fold with physiological saline, and 3.4 mL of methanol and 600 μL of an 8% hydrochloric acid methanol solution were added thereto. After heating at 100° C. for 1 hour, fatty acid methyl ester was extracted by liquid separation using 800 μL of hexane.

(2) The specimen obtained in (1) was subjected to gas chromatography analysis using an Agilent 7890B GC system and an InterCap (registered trademark) WAX column. Calibration curves were formed using methyl myristate, methyl palmitate, methyl Cis-9-hexadecenoate, methyl stearate, and methyl oleate as the standards, and the concentration of each specimen was measured.

(3) Results

As a result, as shown in Table 3, myristic acid, palmitic acid, Cis-9-hexadecenoic acid, stearic acid, and oleic acid were able to be collected. The numerical values in Table 3 indicate the amounts of fatty acids contained in the inventive specimen 4. The aqueous solution of the comparative specimen 2 was not cloudy at all, and thus it was anticipated that collection of fatty acids from the swab was difficult, although fatty acids were not actually quantified.

TABLE 3

| | (μg/mL) |
|---|---|
| Myristic acid | 52.35 |
| Palmitic acid | 188.14 |
| Cis-9-hexadecenoic acid | 176.06 |
| Stearic acid | 39.69 |
| Oleic acid | 148.35 |

Example 5: Preparation of Specimen

One hundred microliters of a PVA solution (PVA: 20%) prepared as in Example 1 was applied to the left forehead (4 $cm^2$). After drying for about 30 minutes, the formed thin-film was peeled. The peeled thin-film was immersed in 1 mL of PBS and was shaken at room temperature for 1 hour to obtain an inventive specimen 5.

Comparative Example 3 (Swab Method)

A swab was reciprocated 25 times on a part (4 $cm^2$) of the central forehead. The tip of the swab was immersed in 1 mL of PBS and was shaken for 1 hour to obtain a comparative specimen 3.

Test Example 5: Analysis of Protein (1) Pretreatment of Specimen

The inventive specimen 5 was subjected to centrifugal washing (15,000 rpm, 20 min) with physiological saline once, and the precipitate was then dissolved in 100 μL of a lysis buffer (20 mM HEPES (pH 7.8), 350 mM NaCl, 0.5 mM EDTA, 0.1 mM EGTA, 1 mM DTT, 1 mM $MgCl_2$, 20% glycerol, 1% NP-40), stirred with a vortex mixer for 10 minutes, and left in an ice bath of 4° C. for 15 minutes. Centrifugation was performed at 15,000 rpm for 20 minutes, and the supernatant was collected and was used for the following measurement.

The comparative specimen 3 was centrifuged at 15,000 rpm for 20 minutes, and the precipitate was dissolved in 100 μL of the lysis buffer, stirred with a vortex mixer for 10 minutes, and left in an ice bath of 4° C. for 15 minutes. Centrifugation was performed at 15,000 rpm for 20 minutes, and the supernatant was collected and was used for the following measurement.

(2) Measurement of Total Protein Amount

The concentration was calculated at absorption wavelength of 562 nm by a BCA protein assay using BSA as the standard.

(3) Measurement of IL-8 Amount

Measurement was performed at absorption wavelength of 450 to 550 nm using a Human IL-8 ELISA kit (manufactured by Thermo Fisher Scientific).

(4) Results

The results are shown in Table 4.

It was confirmed by Table 4 that the amounts of total proteins and IL-8 collected in the inventive specimen 5 were higher than those in the specimen by the swab method and that the inventive specimen 5 is excellent for protein analysis.

TABLE 4

| | Inventive specimen 5 | Comparative specimen 3 |
|---|---|---|
| Total amount of protein (μg/$cm^2$) | 4.81 | 1.57 |
| Amount of IL-8 (pg/$cm^2$) | 0.41 | 0.03 |

Example 6: Preparation of Specimen

A 17.5% PVA solution was prepared according to Example 2. One hundred and fifty microliters of the resulting PVA solution was applied to the forehead (9 cm$^2$, three portions), and 50 μL of the PVA solution was applied to the cheek (3 cm$^2$, 12 portions). After drying for about 30 minutes, the formed thin-films were peeled. The thin-films peeled from the three portions of the forehead and, in the thin-films peeled from the 12 portions of the cheek, three groups each consisting of four thin-films were dissolved or eluted in 1.4 mL of physiological saline, water, and methanol, respectively, and were shaken at room temperature for 1 hour to obtain specimens (physiological saline dissolution specimen, water dissolution specimen, and methanol elution specimen) for analysis.

Test Example 6: Comprehensive Analysis of Ionic Metabolites in Stratum Corneum by CE-TOF MS (1) Measurement was Performed with CE/(Q)TOF MS Manufactured by Agilent Technologies.

Regarding the dilution rates of cations and anions in measurement of each mode, in the cation mode, all specimens were used as undiluted solutions; and in the anion mode, the methanol elution specimens were used as undiluted solutions, and the water dissolution specimens and the physiological saline dissolution specimens were diluted 2-fold.

(2) Results i) Number of Detected Substances

Table 5 shows the numbers of detected ionic metabolites in the specimens. It was confirmed that about 50 types of substances were present in the stratum corneum as the total number of substances detected in the cation and anion modes. In addition, it was confirmed that the anion mode and the cation mode did not detect identical components.

TABLE 5

| | Methanol elution specimen | Water dissolution specimen | Physiological saline dissolution specimen | Total |
|---|---|---|---|---|
| Anion mode | 9 | 7 | 6 | 9 |
| Cation mode | 37 | 42 | 38 | 44 |
| Total | 46 | 49 | 44 | 53 |

The following Table 6 shows substances detected in the water dissolution specimens. It has already been known that large amounts of lactic acid, urea, and glycerol are present in the stratum corneum (H. W. Spier, et al., Zur analytischen and funktionellen Physiologie der Hautoberflache, Der Hautarzt, 7, 55-60, 1956, E. H. Choi, et al., Is Endogeneous glycerol a determinant of stratum corneum hydration in humans., J. Invest. Dermatol., 125, 288-293, 2005), and it was confirmed that all of these substances were detected also in the specimen of the present invention by CE-TOF MS. In addition, regarding amino acids, it was confirmed that all 20 types of amino acids necessary for protein synthesis were detected. Incidentally, "m/z" represents molecular weight divided by charge, and relative area represents the amount of a detected substance.

TABLE 6-1

| Mode | Detected compound | m/z | Relative area in dissolution of specimen in water |
|---|---|---|---|
| Anion | Pyruvic acid | 87.009 | 8.0E−4 |
| | Lactic acid | 89.025 | 1.6E−2 |
| | 5-Oxoproline | 128.035 | 1.0E−3 |
| | Threonic acid | 135.029 | 1.2E−0.5 |
| | Uric acid | 167.021 | 2.5E−5 |
| | Citric acid | 191.019 | 1.1E−4 |
| | Gluconic acid | 195.051 | 1.3E−5 |

TABLE 6-2

| Mode | Detected compound | m/z | Relative area in dissolution of specimen in water |
|---|---|---|---|
| Cation | Urea | 61.041 | 1.7E−2 |
| | Ethanolamine | 62.061 | 1.1E−4 |
| | Glycine | 76.039 | 3.4E−3 |
| | Putrescine | 89.109 | 2.2E−5 |
| | Alanine | 90.055 | 3.6E−3 |
| | Glycerol | 93.055 | 1.9E−2 |
| | Choline | 104.107 | 1.7E−4 |
| | Serine | 106.050 | 8.2E−3 |
| | Diethanolamine | 106.087 | 3.3E−5 |
| | Histamine | 112.087 | 6.1E−5 |
| | Creatinine | 114.066 | 3.5E−5 |
| | 3-Amino-2-piperidone | 115.086 | 3.7E−4 |
| | Proline | 116.071 | 1.6E−3 |
| | Valine | 118.086 | 3.2E−3 |
| | Threonine | 120.065 | 2.5E−3 |
| | Cysteine | 122.027 | 1.8E−5 |
| | Creatine | 132.077 | 5.2E−5 |
| | Isoleucine | 132.101 | 2.7E−3 |
| | Leucine | 132.101 | 3.7E−3 |
| | Asparagine | 133.060 | 5.2E−4 |
| | Ornithine | 133.097 | 1.3E−3 |
| | Aspartic acid | 134.044 | 2.0E−3 |
| | Urocanic acid | 139.050 | 2.3E−3 |
| | Methyl-4-imidazole acetic acid | 141.065 | 6.4E−4 |
| | Stachydrine | 144.101 | 3.1E−5 |
| | Spermidine | 146.165 | 5.6E−6 |
| | Glutamine | 147.076 | 1.3E−3 |
| | Lysine | 147.112 | 1.7E−3 |
| | Glutamic acid | 148.060 | 2.2E−3 |
| | Methionine | 150.058 | 1.9E−4 |
| | Triethanolamine | 150.112 | 1.4E−5 |
| | Histidine | 156.076 | 5.4E−3 |
| | Carnitine | 162.112 | 3.5E−5 |
| | Phenylalanine | 166.085 | 1.5E−3 |
| | Arginine | 175.118 | 4.2E−3 |
| | Citrulline | 176.102 | 3.6E−3 |
| | Tyrosine | 182.080 | 1.0E−3 |
| | ADMA | 203.149 | 2.0E−5 |
| | Tryptophan | 205.096 | 5.4E−4 |
| | Cytidine | 244.093 | 1.3E−5 |
| | Inosine | 269.087 | 1.2E−5 |
| | His-Glu | 285.118 | 1.6E−5 |

Example 7: Preparation of Specimen

A 17.5 mass PVA solution was prepared according to Example 2. Fifty microliters of the PVA solution was applied to an area of 3×1 cm$^2$ of each of the left portions of the antebrachial region and the forehead and was dried for 20 minutes, and the formed thin-films were peeled. The thin-films were affixed to slide glasses to which a silylated urethane resin adhesive ("Ultra High Strength Adhesive Ultra Multi-Use S•U" (manufactured by Konishi Co., Ltd.)) was applied and were dried for 2 days. Subsequently, the slide glasses were gently immersed in Milli-Q water for 12 hours to completely dissolve the PVA. The slide glasses were gently rinsed with Milli-Q water twice and were completely dried to obtain specimens for microscopic observation.

Test Example 7: Observation of Shape of Stratum Corneum

Microscopic observation (optical microscope and electron microscope) was performed using the specimens for microscopic observation obtained in Example 7. FIGS. 1 and 2 show microscopic observation images.

It was confirmed by FIGS. 1 and 2 that texture and hair follicles were reversed on the front and back of the collected stratum corneum.

INDUSTRIAL APPLICABILITY

According to the specimen for skin analysis or observation prepared by the method of the present invention, the resident skin bacterial flora and the substances present in the stratum corneum can be comprehensively analyzed and can be associated with each other. In addition, useful bacteria and unknown bacteria can be isolated in a living state. Since the total amount of proteins that can be collected is high, it becomes easier to analyze proteins. In addition, the conditions of the microstructures of both sides of collected stratum corneum can be visualized in a state viewed from the outside of the skin. As a result, it can be used for the development of cosmetics and the establishment of skin diagnostic technology.

The invention claimed is:

1. A method for preparing a specimen for analyzing a resident skin bacterium and/or a substance present in the stratum corneum, the method comprising:
    applying a solution comprising a polyvinyl alcohol polymer to the skin as a liquid so as to form a thin-film;
    peeling and collecting the formed thin-film; and
    dissolving the formed thin-film in an aqueous solvent to extract the specimen.

2. The method of claim 1, wherein the resident skin bacterium comprises a live bacterium.

3. The method of claim 1, wherein the substance present in the stratum corneum comprises one or more selected from the group consisting of a protein, an amino acid, a lipid, a nucleic acid, a saccharide, a vitamin, a hormone, and a peptide.

4. The method of claim 1, wherein the polyvinyl alcohol polymer is a polyvinyl alcohol polymer having a degree of saponification of 70 to 99 mol %.

5. The method of claim 1, wherein the polyvinyl alcohol polymer is a polyvinyl alcohol polymer having a degree of polymerization of 50 to 3,000.

6. The method of claim 1, wherein the polyvinyl alcohol polymer is a polyvinyl alcohol polymer having a viscosity of 4 to 60 mPa·s in a 4% aqueous solution at 20° C.

7. The method of claim 1, wherein the solution comprises 10 to 30 mass % of the polyvinyl alcohol polymer based on a total mass of the solution.

8. The method of claim 1, wherein the solution comprising the polyvinyl alcohol polymer is applied to the skin and is then left at room temperature for 20 minutes or more.

9. A method for preparing a specimen for observing a shape of a stratum corneum, the method comprising:
    applying a solution comprising a polyvinyl alcohol polymer to the skin as a liquid so as to form a thin-film;
    peeling and collecting the formed thin-film;
    immobilizing the peeled and collected thin-film to a support for microscopic observation,
    dissolving and removing the polyvinyl alcohol polymer, and then performing drying, and
    microscopically observing the specimen for observation of the shape of the stratum corneum.

10. The method of claim 9, wherein the immobilization is performed by affixing the thin-film to an immobilizing agent applied to the support for microscopic observation.

11. The method of claim 9, wherein the polyvinyl alcohol polymer is a polyvinyl alcohol polymer having a degree of saponification of 70 to 99 mol %.

12. The method of claim 9, wherein the polyvinyl alcohol polymer is a polyvinyl alcohol polymer having a degree of polymerization of 50 to 3,000.

13. The method of claim 9, wherein the polyvinyl alcohol polymer is a polyvinyl alcohol polymer having a viscosity of 4 to 60 mPa·s in a 4% aqueous solution at 20° C.

14. The method of claim 9, wherein the solution comprises 10 to 30 mass % of the polyvinyl alcohol polymer based on a total mass of the solution.

15. The method of claim 9, wherein the solution comprising the polyvinyl alcohol polymer is applied to the skin and is then left at room temperature for 20 minutes or more.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 1
gcgtgagtga cggtaatggg ta                                              22

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
ttccgacgcg atcaacca                                                   18
```